United States Patent [19]

Mayer

[11] 3,989,817

[45] Nov. 2, 1976

[54] PREPARATION FOR HARDENING ANIMAL FINGER AND TOENAIL TISSUE AND METHOD

[76] Inventor: Frederick S. Mayer, 1053 Lea Drive, San Rafael, Calif. 94903

[22] Filed: Apr. 14, 1972

[21] Appl. No.: 244,246

Related U.S. Application Data

[63] Continuation-in-part of Ser. No. 816,080, April 14, 1969, abandoned.

[52] U.S. Cl. ................................................ 424/61
[51] Int. Cl.$^2$ .......................................... A61K 7/043
[58] Field of Search ...................................... 424/61

[56]  References Cited
UNITED STATES PATENTS 3,034,966   5/1962   Williams .............................. 424/61

OTHER PUBLICATIONS

Sagarin Cosmetics Science and Technology, 1957, pp. 709 to 711.
Greenberg, et al., 1954, Handbook of Cosmetic Materials, pp. 245 to 247.
Goodman, One Hundred Dermatological Formulas, 1951, pp. 114 and 115.
Achten American Perfumes and Cosmetics, 1964, vol. 79, pp. 23 to 26.
Kirk–Othmer, Encyclopedia of Chemical Technology, 2nd Suppl. vol., 1960, pp. 490 to 492, 495, 512, 513, 519.
Kirk–Othmer, Encycl. of Chem. Tech., 1951, vol. 6 pp. 144 to 147.
Brown et al., U.S. Dispensatory, 1922, Part I, 20th edition, p. 725.

Primary Examiner—Dale R. Ore
Attorney, Agent, or Firm—Warren, Chickering & Grunewald

[57]   ABSTRACT

Animal finger and toenails are hardened and toughened by treatment with walnut oil. The presence of a minor amount of iodide ion promotes the desired action. The application of the oil is conveniently effected by means of a neutral oleaginous carrier.

4 Claims, No Drawings

PREPARATION FOR HARDENING ANIMAL FINGER AND TOENAIL TISSUE AND METHOD

This application is a continuation-in-part of my patent application PREPARATION FOR HARDENING ANIMAL FINGER AND TOENAIL TISSUE AND METHOD, Ser. No. 816,080, filed Apr. 14, 1969, now abandoned.

This invention relates to a preparation for hardening animal finger and toenails, particularly to a novel preparation containing walnut oil in a form convenient for application to animal nails. Still more particularly, it relates to a water-in-oil emulsion containing walnut oil and a minor amount of water soluble iodide salt.

Preparations for the protection and improvement of nails in the cosmetic and practical sense are well known in the art. However, these in general suffer from disadvantages. Some merely provide a superficial coating or overlay on the nail. Others are intended to interact chemically with keratinous tissue and thereby to benefit the user. The cosmetic overlays, laquers and the like, are merely protective so long as intact and bonded to the nail. Basically no change results in the nail proper from the application. Usually the same agents adversely effect the overlay as do the nail and frequent removal and replacement of the overlay are necessary. Chemical nail treating agents for hardening nails ordinarily utilize relatively high concentrations of reactive chemical substances, for example formaldehyde, and are inconvenient to apply since protective shields and devices are required to protect the surrounding tissue from harmful interactions.

I have now found that keratinous tissue, especially a finger or toenail of an animal, is improved by a repetitive treatment with walnut oil. Usually after a daily topical application of the oil, preferably in the form of a water-in-oil emulsion containing a minor amount of potassium iodide, a notable hardening and toughening of the tissue is evident after a period of from one to two weeks. Continued topical applications serve to maintain the desirable characteristics in the nail. Surprisingly, nails and toenails treated with wallnut oil in the aforementioned matter are harder yet not more brittle than in the untreated state. Hence the nails are of improved toughness and hardness and are more resistant to ordinary damage as from unfortuitous physical impacts with hard substances, metals and the like. Apparently, the exceptionally high content of and the variety of unsaturated and polyunsaturated organic carboxylic acids and esters normally present in walnut oil interact chemically with keratinous tissue, particularly in the presence of catalytic amounts of iodide ion, and cause substantial crosslinking of the protein molecule chains present in keratinous (protein-aceous) tissue.

Walnut oil is the active ingredient in the preparations of my invention and may be used per se for the treatment. However, since it is a light oil having a low viscosity and is a highly unsaturated oil which tends to polymerize or darken upon standing, for example unless shielded from light and air, it is preferable that it be suspended in a neutral oil base carrier as in a water-in-oil emulsion. A further advantage of the emulsion form, that is in addition to the improved increased viscosity effect, is that the promoter, a minor amount of a water soluble iodide salt, is for the most part retained in the water phase and out of effective contact with the unsaturated carboxylic acids of the walnut oil. Subsequently, at the time the preparation herein is applied topically to the nail, preferably by a simple working-in of the preparation by ordinary rubbing or kneading for a few minutes, the oil, promoter and keratinous tissue are brought together sufficiently intimately to achieve a useful nail hardening and toughening.

The promoting action herein by an iodide salt appears to be due to iodide ion. Hence a water soluble salt should be used. Representative iodide salts satisfactory for use in the preparations of my invention include the alkali metal, ammonium and quaternary ammonium iodide salts and the like. Potassium iodide is preferred.

An iodide salt (iodide ion) is believed to function as a promoter or a catalyst herein. Accordingly but a relatively minor amount is required for a satisfactory action. For each 100 parts by weight of walnut oil in the preparation an amount of the iodide salt in the range from about 0.001 to 0.1 mol, preferably 0.005 to 0.05, mol should be present in the preparation.

The relative amount of walnut oil which should be present in the preparation varies. Desirably the walnut oil should be sufficiently concentrated in order that a single daily topical application to a nail or toenail will in general cause a useful effect. Accordingly, for each 100 parts by volume of the preparation, an amount of walnut oil in the range from about 10 to 50, preferably 20 to 30, parts by volume is desirably present.

The amount of water desirably present in the preparations herein depends upon several variables, including the carrier, the relative amount of walnut oil in the preparation, and whether or not a suspending agent or emulsifier is employed. In general, a satisfactory amount in parts by volume of water per 100 parts of the preparation will be in the range from 25 to 45 parts, preferably 35 to 40 parts.

Carriers suitable for use herein may vary widely but are in general oleaginous, i.e. oil-like, neutral materials such as sulfuric acid washed and neutralized mineral oil, paraffinic hydrocarbon mixtures, higher ($C_6$ to $C_{20}$) alkanols, saponified wool fat, neutral cream absorption bases as known in the cosmetic art, mixtures of the foregoing and the like, e.g., a neutral oleaginous carrier selected from the group consisting of mineral oil, paraffinic hydroccarbon mixtures $C_6$–$C_{20}$-alkanols, saponified wool fat, and mixtures thereof. I prefer to employ a neutral cream base as known in the cosmetic art, for example the commercial absorption base known in the trade as Aquaphor, because such have been established as satisfactory for use as inert carriers where contact is to be made with human skin. Although such oleaginous materials are frequently noted for their softening action upon skin tissue, nevertheless, no comparable undesirable action is evident upon nail-like keratinous tissue, when a neutral cream base is used as a carrier for walnut oil as herein.

The amount of oleaginous carrier desirably used will be in the range 25 to 45 parts per 100 parts by volume of the preparation, preferably 30 to 40 parts.

Suspending or emulsifying agents may be used in the manner known in the art. For example, a minor amount of a nonionic surface active agent added to the mixture may be helpful (see, for example, Encyclopedia of Chemical Technology, Second Supplement, R. E. Kirk Interscience Publisher (1960), pp. 490–519, 519) in improving the stability of the emulsion.

For the preparation of a water-in-oil emulsion as herein, conventional techniques as known and used in the art are in general satisfactory and contemplated, including the use of thickening agents, high speed stirring, high sheer mixers and the like.

Walnut oil is a well known and available commodity. While its composition may vary moderately depending upon the source of the nuts and the processing of the oil, commercially available walnut oils are in general satisfactory for use in my preparations and method. Representative characterizations of walnut oil are in the art, for example in the Encyclopedia of Chemical Technology, R. E. Kirk, Volume 6 (1951), page 144.

The following example further illustrates my invention.

EXAMPLE

A water-in-oil emulsion (a cream) was prepared by efficiently mixing the following ingredients:

| Component | Amount, Vol. Percent |
| --- | --- |
| Walnut oil | 26.0 |
| Inert carrier[1] | 39.2 |
| Aqueous potassium iodide[2] | 4.4 |
| Water | 30.4 |

[1]Aquaphor: 6 parts (volume) saponified wool fat plus 94 parts (volume) of paraffinic hydrocarbon - melting point 48° C. to 55° C.
[2]A saturated or concentrated solution (ambient temperature), i.e. about 4.4 parts (weight) of water and 2 parts (weight) of KI (ca. 0.06 mol of KI per 100 parts by weight of the carrier).

The resulting mixture was a stable emulsion which maintained its texture and shape under ordinary ambient temperatures, i.e. similar to an ordinary cosmetic face cream. When a daily topical application of this cream was placed upon finger nails and applied by rubbing or massaging the cream into the nails for several minutes, the nails were found after a period of about one week to be appreciably hardened and toughened relative to the previously untreated nails. Further hardening of the nails has been observed with continued daily usage.

Other inert carriers and water soluble iodide salts as described above may also be advantageously employed to prepare relatively solid emulsions or liquid lotions useful for treating animal finger and toenails.

A surprising result of the use of the aforementioned nail hardening preparation is that it has been found satisfactory for users who in the ordinary course of their employment immerse their hands in peroxide, dyes, bleaches, and heavy alkaline solutions which would tend to cause the nails to crack, soften, split, or peel. Also, surprisingly satisfactory results have been obtained with users who play musical instruments such as guitars and the like where the fingernails are exposed to particularly heavy duty in the striking of strings which often cause the nails to break, split, and peel.

Although the foregoing specification has set forth my invention with particular detail, this has been done for purposes of illustration and not to impose unnecessary limitations upon my invention which may be practiced in a variety of forms within the scope of the appended Claims.

I claim:

1. The composition suitable for use for the hardening of keratinous animal finger or toenail tissue consisting essentially of a mixture of walnut oil, water and a neutral oleaginous carrier wherein in parts by volume for each 100 parts of the mixture there is present an amount of walnut oil in the range from 10 to 50 parts, an amount of water in the range 25 to 45 parts and an amount of the carrier in the range 25 to 45 parts, said carrier being selected from the group consisting of mineral oil, paraffinic hydrocarbon mixtures, $C_6$–$C_{20}$-alkanols, saponified wool fat, and mixtures thereof.

2. The composition as in claim 1 wherein said mixture contains for each 100 parts by weight of the walnut oil an amount of a water soluble iodide salt in the range from about 0.001 to 0.1 mol, said salt being selected from the group consisting essentially of alkali metal, ammonium and quaternary ammonium iodide salts, said amount of the iodide salt being sufficient to promote hardening of keratinous nail tissue by walnut oil.

3. The composition as in claim 1 wherein the amount of walnut oil is in the range 20 to 30 parts, and the amounts of water and carrier are each in the range 30 to 40 parts, wherein for each 100 parts by weight of walnut oil said mixture contains an amount of potassium iodide in the range from about 0.005 to 0.05 mol.

4. The composition suitable for use for the hardening of keratinous animal finger or toenail tissue consisting essentially of a mixture of about 26 volume percent of walnut oil, about 39 volume percent of an inert carrier, about 35 volume percent of water and about 0.06 mol of potassium iodide per 100 parts by weight of the carrier, said carrier being a neutral oleaginous mixture in parts by volume of saponified wool fat and paroffinic hydrocarbon in the ratio of about 6 to 94, respectively.

* * * * *